United States Patent [19]

Butler

[11] 4,454,327

[45] Jun. 12, 1984

[54] 5-OXO-2,2-PYRROLIDINEDIPROPANOIC ACID AND ESTER DERIVATIVES THEREOF

[75] Inventor: Donald E. Butler, Ann Arbor, Mich.

[73] Assignee: Warner-Lambert Company, Morris Plains, N.J.

[21] Appl. No.: 381,483

[22] Filed: May 24, 1982

[51] Int. Cl.$^3$ ............... C07D 207/273; A61K 31/40
[52] U.S. Cl. ............................. 548/551; 424/274; 548/452
[58] Field of Search ........................ 548/551

[56] References Cited

U.S. PATENT DOCUMENTS 2,502,548  4/1950  Allen et al. .................. 548/551

FOREIGN PATENT DOCUMENTS 53-5158  1/1978  Japan ......................... 548/551

Primary Examiner—Paul M. Coughlan, Jr.
Assistant Examiner—D. B. Springer
Attorney, Agent, or Firm—Jerry F. Janssen

[57] ABSTRACT

5-oxo-2,2-pyrrolidinedipropanoic acid, base addition salts and esters are useful as agents for the reversal of amnesia. Intermediates for preparing said compounds, pharmaceutical compositions containing said compounds and methods for using said pharmaceutical compositions for treating senility and reversal of amnesia are also taught.

8 Claims, No Drawings

5-OXO-2,2-PYRROLIDINEDIPROPANOIC ACID AND ESTER DERIVATIVES THEREOF

BACKGROUND OF THE INVENTION

The synthesis of 5-oxo-2,2-pyrrolidinedipropanoic acid and the corresponding diethyl ester is reported in U.S. Pat. No. 2,502,548 and British Pat. No. 610,304. The compounds are utilized in the references as chemical intermediates for polymers.

SUMMARY OF THE INVENTION p The invention sought to be patented in a first generic chemical compound aspect is a compound having the structural formula I

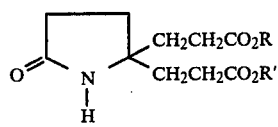

wherein R and R' are the same or different and are hydrogen;

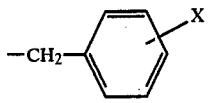

wherein X is hydrogen, alkyl of from one to six carbon atoms, alkoxy of from one to six carbon atoms, halo or trifluoromethyl; alkyl having from one to six carbon atoms; or a pharmaceutically acceptable metal or amine cation; provided that R and R' may not both be hydrogen, ethyl, or different pharmaceutically acceptable metal or amine cations.

The invention sought to be patented in a subgeneric aspect of its first chemical compound aspect is a compound having the structural formula I wherein R and R' are the same; provided they are not hydrogen or ethyl.

The invention sought to be patented in a first specific aspect of its first generic chemical compound aspect is the compound having the name 5-oxo-2,2-pyrrolidinedipropanoic acid disodium salt.

The invention sought to be patented in a second specific aspect of its first generic chemical compound aspect is the compound having the name 5-oxo-2,2-pyrrolidinedipropanoic acid dibenzyl ester.

The invention sought to be patented in a second subgeneric chemical compound aspect is a compound having the structural formula II

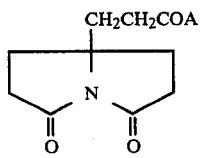

wherein A is chlorine, bromine, or

wherein $R_a$ is alkyl of from one to six carbon atoms.

The invention sought to be patented in a first specific aspect of its second generic chemical compound aspect is the compound having the name tetrahydro-3,5-dioxo-1H-pyrrolizine-7a(5H)-propanoyl chloride.

The invention sought to be patented in a second specific aspect of its second generic chemical compound aspect is the compound having the name tetrahydro-3,5-dioxo-1H-pyrrolizine-7a(5H)-propanoic acid anhydride with acetic acid.

The invention sought to be patented in its pharmaceutical composition aspect is a composition which comprises a compound having the structural formula III

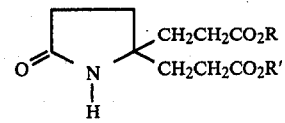

wherein R and R' are the same or different and are hydrogen;

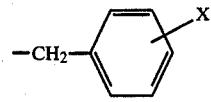

wherein X is hydrogen, alkyl of from one to six carbon atoms, alkoxy of from one to six carbon atoms, halo or trifluoromethyl; alkyl having from one to six carbon atoms; or a pharmaceutically acceptable metal or amine cation; in combination with a pharmaceutically acceptable carrier; provided that R and $R_1$ may not be different pharmaceutically acceptable metal or amine cations.

The invention sought to be patented in a subgeneric pharmaceutical composition aspect is a composition which comprises a compound having the structural formula III wherein R and R' are the same.

The invention sought to be patented in a first specific pharmaceutical composition aspect is a composition which comprises 5-oxo-2,2-pyrrolidinedipropanoic acid, in combination with a pharmaceutically acceptable carrier.

The invention sought to be patented in a second specific pharmaceutical composition aspect is a composition which comprises 5-oxo-2,2-pyrrolidinedipropanoic acid diethyl ester in combination with a pharmaceutically acceptable carrier.

The invention sought to be patented in a third specific pharmaceutical composition aspect is a composition which comprises 5-oxo-2,2-pyrrolidinedipropanoic acid dibenzyl ester in combination with a pharmaceutically acceptable carrier.

The invention sought to be patented in its pharmaceutical method aspect is a method for treating senility or for reversing amnesia, which method comprises administering an effective amount of the above defined pharmaceutical composition to a mammal in need thereof.

The invention sought to be patented in its chemical process aspect is a process for preparing a compound having the structural formula I which comprises treating a compound having the structural formula

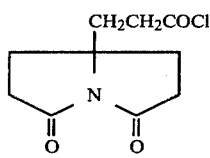

with one molar equivalent of a compound having the formula ROH in the presence of an acid acceptor, and treating the compound thus formed with one molar equivalent of a compound having the formula R'OH.

DESCRIPTION OF THE PREFERRED EMBODIMENTS

The symmetrical compounds of formula I, those wherein R and R' are the same, compounds $I_S$; may be conveniently prepared from the known compound 5-oxo-2,2-pyrrolidinedipropanoic acid by the following procedure:

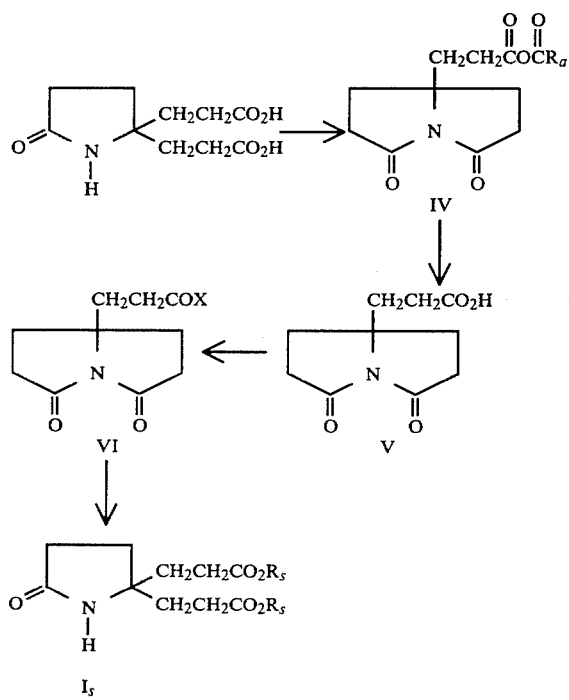

Compound IV wherein $R_a$ is an alkyl group of from one to six carbon atoms is prepared by heating 5-oxo-2,2-pyrrolidinedipropanoic acid with a compound of the formula $(R_aCO)_2O$. In the preferred procedure, the diacid is heated to about 100° C. for 24 hours in acetic anhydride ($R_a$=CH$_3$). The so produced compound IV is then treated water to produce the acid V. This treatment may be carried out at room temperature by stirring IV vigorously in water either alone or in the presence of a water miscible solvent such as acetonitrile. The acid V is then converted to the acid halide VI, wherein X represents chlorine or bromine, in a conventional manner. For example, a suspension of V in a convenient solvent such as methylene chloride is treated at room temperature with a halogenating agent in the presence of a catalytic amount of a base such as pyridine to produce VI. The preferred halogenating agent is thionyl chloride which produces the acid chloride, i.e., compound VI wherein x is chlorine. Compound VI is then treated with an excess of a compound $R_SOH$ at about 25°–60° C. to produce the compounds of formula $I_S$, i.e., compounds of formula I wherein R and R' are the same. It will be clear to those skilled in the art that the group $R_S$, is identical to the groups R and R' as defined above. The compounds $I_S$, wherein $R_S$ is a pharmaceutically acceptable metal or amine cation may also be prepared directly from 5-oxo-2,2-pyrrolidinedipropanoic acid by treatment with at least two equivalents of the desired pharmaceutically acceptable base.

The nonsymmetrical compounds of formula I, those wherein R and R' are different, Compounds $I_d$; may be conveniently prepared from the acid halide VI. In the preferred procedure, the acid chloride (Compound VI wherein X is chlorine) is treated with one mole of a compound ROH in the presence of a suitable acid acceptor such as triethylamine or pyridine to produce the ester VII.

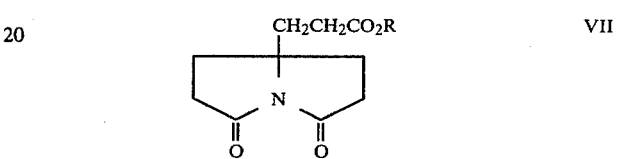

Ester VII is then treated with one mole of a compound R'OH to produce the desired unsymmetrical compounds $I_d$, i.e., compounds I wherein R and R' are different. Those skilled in the art will recognize that the order of reaction will not affect the structure of the final compound; thus compound VI may first be treated with R'OH in the presence of an acid acceptor and the product of this reaction then may be treated with ROH to similarly produce compounds $I_d$. It is believed that the compounds $I_d$ wherein R and R' are different pharmaceutically acceptable metal or amine cations will exist under suitable conditions for example in solution, but will not be readily isolable in pure form.

The compounds having structural formula I wherein R and for R' are hydrogen form pharmaceutically acceptable salts with organic and inorganic bases. Examples of suitable inorganic bases for salt formation are sodium hydroxide, potassium hydroxide, sodium carbonate, calcium carbonate, potassium carbonate, sodium bicarbonate, and the like.

The term pharmaceutically acceptable amine cation contemplates the positively charged ammonium ion and analogous ions derived from organic nitrogenous bases strong enough to form such cations. Bases useful for the purpose of forming pharmacologically-acceptable nontoxic addition salts of such compounds containing free carboxyl groups form a class whose limits are readily understood by those skilled in the art. Merely for illustration, they can be said to comprise, in cationic form, those of the formula:

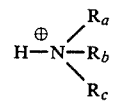

wherein $R_a$, $R_b$, and $R_c$, independently, are hydrogen, alkyl of from about one to about six carbon atoms, cycloalkyl of from about three to about six carbon atoms, aryl of about six carbon atoms, aralkyl of from about 7 to about 11 carbon atoms, hydroxyalkyl of from about two to about four carbon atoms, or monoarylhydroxyalkyl of from about 8 to about 15 carbon atoms, or, when taken together with the nitrogen atom to which they are attached, any two of $R_a$, $R_b$, and $R_c$ may form part of a 5 to 6-membered heterocyclic ring containing carbon, hydrogen, oxygen, or nitrogen, said heterocyclic rings and said aryl groups being unsubstituted or mono- or dialkyl substituted said alkyl groups containing from about one to about six carbon atoms. Illustrative therefore of $R_a$, $R_b$, and $R_c$ groups comprising pharmacologically-acceptable cations derived from ammonia or a basic amine are ammonium, mono-, di-, and trimethylammonium, mono-, di- and triethylammonium, mono-, di-, and tripropylammonium (iso and normal), ethyldimethylammonium, benzyldimethylammonium, cyclohexylammonium, benzylammonium, dibenzylammonium, piperidinium, morpholinium, pyrrolidinium, piperazinium, 1-methylpiperidinium, 4-ethylmorpholinium, 1-isopropylpyrrolidinium, 1,4-dimethylpiperazinium, 1-n-butylpiperidinium, 2-methylpiperidinium, 1-ethyl-2-methylpiperidinium, mono-, di- and triethanolammonium, ethyldiethanolammonium, n-butylmonoethanolammonium, tris(hydroxymethyl)methylammonium, phenylmonoethanolammonium, and the like.

The term, pharmaceutically acceptable metal cation contemplates the positively charged ions derived from such metals as sodium, potassium, calcium, magnesium, aluminum, zinc, iron, and the like. The salts are prepared by contacting the free form of the compound with the proper amount of the desired base in the conventional manner. The free forms may be regenerated by treating the salt form with an acid. For example, dilute aqueous acid solutions may be utilized to regenerate the free form from a respective salt. Dilute aqueous hydrochloric acid is suitable for this purpose. The free forms differ from their respective salt forms somewhat in certain physical properties such as solubility in polar solvents, but the salts are otherwise equivalent to their respective free base forms for purposes of the invention.

The compounds of the invention can exist in unsolvated as well as solvated forms, including hydrated forms. In general, the solvated forms, with pharmaceutically acceptable solvents such as water, ethanol, and the like are equivalent to the unsolvated forms for purposes of the invention.

The alkyl groups contemplated by the invention unless otherwise stated, comprise both straight and branched carbon chains of from one to about six carbon atoms. Representative of such groups are methyl, ethyl, isopropyl, pentyl, 3-methylpentyl, and the like.

For preparing pharmaceutical compositions from the compounds described by this invention, inert, pharmaceutically acceptable carriers can be either solid or liquid. Solid form preparations include powders, tablets, dispersible granules, capsules, cachets, and suppositories. A solid carrier can be one or more substances which may also act as diluents, flavoring agents, solublizers, lubricants, suspending agents, binders or tablet disintegrating agents; it can also be encapsulating material. In powders, the carrier is a finely divided solid which is in admixture with the finely divided active compound. In the tablet the active compound is mixed with carrier having the necessary binding properties in suitable proportions and compacted in the shape and size desired. The powders and tablets preferably contain from 5 to 10 to about 70 percent of the active ingredient. Suitable solid carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as carrier providing a capsule in which the active component (with or without other carriers) is surrounded by carrier, which is thus in association with it. Similarly, cachets are included. Tablets, powders, cachets, and capsules can be used as solid dosage forms suitable for oral administration.

For preparing suppositories, a low melting wax such as a mixture of fatty acid glycerides or cocoa butter is first melted, and the active ingredient is dispersed homogeneously therein as by stirring. The molten homogeneous mixture is then poured into convenient sized molds, allowed to cool and thereby to solidify.

Liquid form preparations include solutions, suspensions, and emulsions. As an example may be mentioned water or water propylene glycol solutions for parenteral injection. Liquid preparations can also be formulated in solution in aqueous polyethylene glycol solution. Aqueous solutions suitable for oral use can be prepared by dissolving the active component in water and adding suitable colorants, flavors, stabilizing and thickening agents as desired. Aqueous suspensions suitable for oral use can be made by dispersing the finely divided active component in water with viscous material, i.e., natural or synthetic gums, resins, methylcellulose, sodium carboxymethylcellulose, and other well-known suspending agents.

Also included are solid form preparations which are intended to be converted, shortly before use, to liquid form preparations for either oral or parenteral administration. Such liquid forms include solutions, suspensions, and emulsions. These particular solid form preparations are most conveniently provided in unit dose form and as such as used to provide a single liquid dosage unit. Alternately, sufficient solid may be provided so that after conversion to liquid form, multiple individual liquid doses may be obtained by measuring predetermined volumes of the liquid form preparation as with a syringe, teaspoon, or other volumetric container. When multiple liquid doses are so prepared, it is preferred to maintain the unused portion of said liquid doses at low temperature (i.e., under refrigeration) in order to retard possible decomposition. The solid form preparations intended to be converted to liquid form may contain, in addition to the active material, flavorants, colorants, stabilizers, buffers, artificial aand natural sweeteners, dispersants, thickeners, solubilizing agents, and the like. The liquid utilized for preparing the liquid form preparation may be water, isotonic water, ethanol, glycerine, propylene glycol, and the like as well as mixtures thereof. Naturally, the liquid utilized will be chosen with regard to the route of administration, for example, liquid preparations containing large amounts of ethanol are not suitable for parenteral use.

Preferably, the pharmaceutical preparation is in unit dosage form. In such form, the preparation is subdivided into unit doses containing appropriate quantities of the active component. The unit dosage form can be a packaged preparation, the package containing discrete quantities of preparation, for example, packeted tablets, capsules, and powders in vials or ampoules. The unit dosage form can also be a capsule, cachet, or tablet itself or it can be the appropriate number of any of these in packaged form.

The quantity of active compound in a unit dose of preparation may be varied or adjusted from 1 mg to 500 mg preferably to 5 to 100 mg according to the particular application and the potency of the active ingredient. The compositions can, if desired, also contain other compatable therapeutic agents.

In therapeutic use as cognition activators, the mammalian dosage range for a 70 kg subject is from 1 to 1500 mg/kg of body weight per day or preferably 25 to 750 mg/kg of body weight per day. The dosages, however, may be varied depending upon the requirements of the patient, the severity of the condition being treated, and the compound being employed. Determination of the proper dosage for a particular situation is within the skill of the art. Generally, treatment is initiated with smaller dosages which are less than the optimum dose of the compound. Thereafter the dosage is increased by small increments until the optimum effect under the circumstances is reached. For convenience, the total daily dosage may be divided and administered in portions during the day if desired.

The effectiveness of the aforementioned compounds was determined by the test designed to show the compound's ability to reverse amnesia produced by electroconvulsive shock. The test is fully described in U.S. Pat. No. 4,145,347, issued March 20, 1979, and is herein incorporated by reference. The test compounds in the present instance were administered orally.

The following criteria are used in interpreting the percent of amnesia reversal scores: 40 percent or more (active=A) 25 to 39 percent (borderline=C) and 0 to 24 percent (inactive=N).

Table 1 below reports the percent of amnesia reversal of orally administered 5-oxo-2,2-pyrrolidinedipropanoic acid.

TABLE 1

| Dose mg/kg | 0.63 | 1.25 | 2.50 | 5.00 | 20.00 | 80.00 |
|---|---|---|---|---|---|---|
| % Reversal | 17 | 42 | 25 | 93 | 36 | 50 |
| Rating | N | A | C | A | C | A |

Table 2 below reports the percent of amnesia reversal of orally administered 5-oxo-2,2-pyrrolidindipropanoic acid esters.

TABLE 2

| R Group of Esters | Dose in mg/kg % Reversal (Rating) | | | |
|---|---|---|---|---|
| | 2.50 | 5.00 | 20.00 | 80.00 |
| $C_2H_5$ | 33(C) | 62(A) | 62(A) | 62(A) |
| $CH_2Ph$ | | 8(N) | 18(N) | 64(A) |
| $CH_2Ph(O-Cl)$ | | 25(C) | 38(C) | 31(C) |

CHEMICAL COMPOSITIONS

EXAMPLE A

Preparation of Tetrahydro-3,5-dioxo-1H-pyrrolizine-7a(5uns/H/)propanoic acid

A solution of 160 g of crude γ-carbomethoxyethyl-γ-nitropimelic acid dimethyl ester in 800 ml of methanol is hydrogenated at approximately 50 psi using 2 g of 20% Pd/C as catalyst. The resulting slurry is filtered to remove the catalyst and the filtrate is concentrated at reduced pressure to yield crude 5-oxo-2,2-pyrrolidinedipropanoic acid methyl ester and 5-oxo-2,2-pyrrolidinedipropionic acid monomethyl ester. The crude esters are dissolved in 100 ml of methanol and 100 ml of water and are treated with 120 g of 50% sodium hydroxide solution. The reaction mixture is stirred and is heated to 100° C. with distillation of methanol.

The solution is cooled, neutralized with 130 ml of concentrated hydrochloric acid and concentrated at reduced pressure. The residue containing 5-oxo-2,2-pyrrolidinedipropanoic acid is heated at 98°–100° C. for 24 hours with 204 g of acetic anhydride. The sodium chloride is removed by filtration after the acetic anhydride reaction. The filtrate is then concentrated at reduced pressure and 200 ml of toluene is added and concentration is repeated. The resulting oil is crude tetrahydro-3,5-dioxo-1H-pyrrolizine-7a(5H)-propanoic acid anhydride with acetic acid. The oil is stirred vigorously with water or is reacted with water in acetonitrile and the tetrahydro-3,5-dioxo-1H-pyrrolizine-7a(5H)-propanoic acid is isolated by filtration.

EXAMPLE B

Preparation of Tetrahydro-3,5-dioxo-1H-pyrrolizine-7a(5H)-propanoyl chloride

A suspension of 10 g (0.048 mole) of tetrahydro-3,5-dioxo-1H-pyrrolizine-7a(5H)-propanoic acid in 250 ml of dichloromethane is treated with 12 g (0.1 mole) thionyl chloride and 1 drop of pyridine. The mixture is stirred for 16 hours at room temperature and concentrated at reduced pressure to an oil that crystallizes upon standing. The tetrahydro-3,5-dioxo-1H-pyrrolizine-7a(5H)-propanoyl chloride is used without further purification.

EXAMPLE C

Preparation of 5-Oxo-2,2-pyrrolidinedipropanoic acid

A solution of 10 g (0.0437 mole) of tetrahydro-3,5-dioxo-1H-pyrrolizine-7a(5H)-propanoyl chloride in 100 ml of water is stirred vigorously for 16 hours at 50° C. The solution is concentrated at reduced pressure and the resulting 5-oxo-2,2-pyrrolidinedipropanoic acid crystallizes and is isolated by filtration. The product is dried in vacuo and has a melting point of 162°–164° C.

EXAMPLE D

Preparation of 5-Oxo-2,2-pyrrolidinedipropanoic acid dimethyl ester.

A solution of 10 g (0.0437 mole) of tetrahydro-3,5-dioxo-1H-pyrrolizine-7a(5H)-propanoyl chloride in 100 ml of methanol is stirred vigorously for 16 hours at 50° C. The solution is concentrated at reduced pressure and the resulting 5-oxo-2,2-pyrrolidinedipropanoic acid dimethyl ester crystallizes and is isolated by filtration. The product is dried in vacuo and has a melting point of 70°–73° C.

EXAMPLE E

Preparation of 5-Oxo-2,2-pyrrolidinedipropanoic acid diethyl ester.

A solution of 10 g (0.0437 mole) of tetrahydro-3,5-dioxo-1H-pyrrolizine-7a(5H)-propanoyl chloride in 100 ml of ethanol is stirred vigorously for 16 hours at 50° C. The solution is concentrated at reduced pressure and the resulting 5-oxo-2,2-pyrrolidinedipropanoic acid diethyl ester crystallizes and is isolated by filtration. The product is dried in vacuo and has a melting point of 44°–46° C.

EXAMPLE F

Preparation of 5-Oxo-2,2-pyrrolidinedipropanoic acid dibenzyl ester.

A solution of 10 g (0.0437 mole) of tetrahydro-3,5-dioxo-1H-pyrrolizine-7a(5H)-propanoyl chloride in 100 ml of benzyl alcohol is stirred 3 hours at 25° C. The mixture is concentrated at reduced pressure and the resulting oil is chromatographed over silica gel in dichloromethane. Elution with 40% anhydrous diethyl ether in dichloromethane removes the 5-oxo-2,2-pyrrolidinedipropanoic acid dibenzyl ester from the silica gel. The solution is concentrated at reduced pressure and the 5-oxo-2,2-pyrrolidinedipropanoic acid dibenzyl ester crystallizes upon standing and after washing with anhydrous diethyl ether and drying has a melting point of 60°–62° C.

EXAMPLE G

Preparation of 5-Oxo-2,2-pyrrolidinedipropanoic acid di-p-chlorobenzyl ester.

A solution of 10 g (0.0437 mole) of tetrahydro-3,5-dioxo-1H-pyrrolizine-7a(5H)-propanoyl chloride in 100 ml of p-chlorobenzyl alcohol is stirred for three hours at 25° C. The mixture is concentrated at reduced pressure and the resulting oil is chromatographed over silica gel in dichloromethane. Elution with 25% anhydrous diethyl ether in dichloromethane removes the 5-oxo-2,2-pyrrolidinedipropanoic acid di-p-chlorobenzyl ester from the silica gel. The solution is concentrated at reduced pressure and the 5-oxo-2,2-pyrrolidinedipropanoic acid di-p-chlorobenzyl ester crystallizes upon standing with a melting point of 74°–75° C.

EXAMPLE H

Preparation of 5-Oxo-2,2-pyrrolidinedipropanoic acid di-o-chlorobenzyl ester.

A solution of 10 g (0.0437 mole) of tetrahydro-3,5-dioxo-1H-pyrrolizine-7a(5H)-propanoyl chloride in 100 ml of o-chlorobenzyl alcohol is stirred for three hours at 25° C. The mixture is concentrated at reduced pressure and the resulting oil is chromatographed over silica gel in dichloromethane. Elution with 25% anhydrous diethyl ether in dichloromethane removes the 5-oxo-2,2-pyrrolidinedipropanoic acid di-o-chlorobenzyl ester from the silica gel. The solution is concentrated at reduced pressure and the 5-oxo-2,2-pyrrolidinedipropanoic acid di-o-chlorobenzyl ester crystallizes upon standing with a melting point of 100°–102° C.

The invention is further illustrated by the following examples of tablets containing 1.0, 2.5, 25, 50 mg, capsules containing 1.0, 2.5, 25, 50 mg respectively of active component, an example of a parenteral formulation, an example of a suppository for rectal administration, an example of a suspension formulation, and an example of a syrup for reconstitution formulation for oral administration.

PHARMACEUTICAL COMPOSITIONS

EXAMPLE 1

| Ingredient | Quantity |
| --- | --- |
| 5-Oxo-2,2-pyrrolidinedipropanoic acid | 150 g |
| Lactose | 1124 g |
| Corn Starch | 39 g |
| Hydroxypropylcellulose | 30 g |
| Magnesium stearate | 7 g |
| Ethanol-water 50:50 | qs |

The 5-oxo-2,2-pyrrolidinedipropanoic acid, lactose, and hydroxypropylcellulose are blended and granulated with 50:50 ethanol-water. The wet granulation is screened, dried, and rescreened. The resulting dried granulation is blended with magnesium stearate and the corn starch and the mixture is compressed into 225 mg tablets using an 11/32 inch standard concave punch. Yield equals approximately 6000 tablets each containing 25.0 mg of 5-oxo-2,2-pyrrolidinedipropanoic acid.

EXAMPLE 2

| Ingredient | Quantity |
| --- | --- |
| 5-Oxo-2,2-pyrrolidinedipropanoic acid | 15 g |
| Lactose | 1249 g |
| Corn Starch | 39 g |
| Hydroxypropylcellulose | 30 g |
| Magnesium stearate | 7 g |
| Ethanol-water 50:50 | qs |

The 5-oxo-2,2-pyrrolidinedipropanoic acid, lactose, and hydroxypropylcellulose are blended and granulated with 50:50 ethanol-water. The wet granulation is screened, dried, and rescreened. The resulting dried granulation is blended with magnesium stearate and the corn starch, and the mixture is compressed into 225 mg tablets using an 11/32 inch standard concave punch. Yield equals approximately 6000 tablets each containing 2.5 mg of 5-oxo-2,2-pyrrolidinedipropanoic acid.

EXAMPLE 3

| Ingredient | Quantity |
| --- | --- |
| 5-Oxo-2,2-pyrrolidinedipropanoic acid | 6 g |
| Lactose | 1268 g |
| Corn Starch | 39 g |
| Hydroxypropylcellulose | 30 g |
| Magnesium stearate | 7 g |
| Ethanol-water 50:50 | qs |

The 5-oxo-2,2-pyrrolidinedipropanoic acid, lactose, and hydroxypropylcellulose are blended and granulated with 50:50 ethanol-water. The wet granulation is screened, dried, and rescreened. The resulting dried granulation is blended with magnesium stearate and the corn starch and the mixture is compressed into 225 mg tablets using an 11/32 inch standard concave punch. Yield equals approximately 6000 tablets each containing 1.0 mg of 5-oxo-2,2-pyrrolidinedipropanoic acid.

EXAMPLE 4

| Ingredient | Quantity |
| --- | --- |
| 5-Oxo-2,2-pyrrolidinedipropanoic acid | 300 g |
| Lactose | 974 g |
| Corn Starch | 39 g |
| Hydroxypropylcellulose | 30 g |
| Magnesium stearate | 7 g |
| Ethanol-water 50:50 | qs |

The 5-oxo-2,2-pyrrolidinedipropanoic acid, lactose, and hydroxypropylcellulose are blended and granulated with 50:50 ethanol-water. The wet granulation is screened, dried, and rescreened. The resulting dried granulation is blended with magnesium stearate and the corn starch, and the mixture is compressed into 225 mg tablets using an 11/32 inch standard concave punch. Yield equals approximately 6000 tablets each containing 50.0 mg of 5-oxo-2,2-pyrrolidinedipropanoic acid.

EXAMPLE 5

| Ingredient | Quantity |
| --- | --- |
| 5-Oxo-2,2-pyrrolidinedipropanoic acid | 250 g |
| Lactose | 1723 g |
| Magnesium stearate | 27 g |

The mixture is blended and filled into No. 4 hard gelatin capsules, filling each capsule with 200 mg of the powder mixture. Yield equals approximately 10,000 capsules each containing 25.0 mg of 5-oxo-2,2-pyrrolidinedipropanoic acid.

EXAMPLE 6

| Ingredient | Quantity |
| --- | --- |
| 5-Oxo-2,2-pyrrolidinedipropanoic acid | 25 g |
| Lactose | 1948 g |
| Magnesium stearate | 27 g |

The mixture is blended and filled into No. 4 hard gelatin capsules, filling each capsule with 200 mg of the powder mixture. Yield equals approximately 10,000 capsules each containing 2.5 mg of 5-oxo-2,2-pyrrolidinedipropanoic acid.

EXAMPLE 7

| Ingredient | Quantity |
| --- | --- |
| 5-Oxo-2,2-pyrrolidinedipropanoic acid | 10 g |
| Lactose | 1963 g |
| Magnesium stearate | 27 g |

The mixture is blended and filled into No. 4 hard gelatin capsules, filling each capsule with 200 mg of the powder mixture. Yield equals approximately 10,000 capsules each containing 1.0 mg of 5-oxo-2,2-pyrrolidinedipropanoic acid.

EXAMPLE 8

| Ingredient | Quantity |
| --- | --- |
| 5-Oxo-2,2-pyrrolidinedipropanoic acid | 500 g |
| Lactose | 1473 g |
| Magnesium stearate | 27 g |

The mixture is blended and filled into No. 4 hard gelatin capsules, filling each capsule with 200 mg of the powder mixture. Yield equals approximately 10,000 capsules each containing 50.0 mg of 5-oxo-2,2-pyrrolidinedipropanoic acid.

The invention is further illustrated by the following example of a 2 gram rectal suppository. Such a suppository can contain a range of from 30 mg to 500 mg of the active component.

EXAMPLE 9

| Ingredient | Quantity |
| --- | --- |
| 5-Oxo-2,2-pyrrolidinedipropanoic acid | 30 mg |
| Witepsol H 35 | 1.97 g |

The Witepsol H 35 is melted by heating to 38° C., the 5-oxo-2,2-pyrrolidinedipropanoic acid is added and mixed thoroughly until dispersed and placed in a mold at 33°–34° C.

The invention is further illustrated by the following example of a suspension formulation. The suspension can contain a range of active ingredient from 50 mg/5 ml to 1 g/5 ml.

EXAMPLE 10

| Ingredient | Quantity |
| --- | --- |
| 5-Oxo-2,2-pyrrolidinedipropanoic acid | 10 g |
| Saccharin Sodium | 0.5 g |
| Trihydroxystearin | 0.75 g |
| Propylparaben | 0.1 g |
| Imitation Cherry Flavor | 2 ml |
| Neobee M-5 q.s. ad | 100 ml |

Propylparaben is dissolved in a portion of the Neobee M-5, the trihydroxystearin is added and the mixture is homogenized for 30 minutes while maintaining the temperature between 50°–60° C. The mixture is cooled and the 5-oxo-2,2-pyrrolidinedipropanoic acid, saccharin sodium, and Imitation Cherry Flavor are added. The volume is made up with Neobee M-5.

The invention is further illustrated by the following example of a Syrup for Reconstitution. The syrup can contain between 50 mg/5 ml and 500 mg/5 ml.

EXAMPLE 11

| Ingredient | Quantity |
| --- | --- |
| 5-Oxo-2,2-pyrrolidinedipropanoic acid | 10 g |
| Sugar granulated, Bottlers grade | 60 g |
| Artificial Peppermint Flavor, Water soluble | 0.4 g |
| Water q.s. ad | 100 ml |

EXAMPLE 12

| Ingredient | Quantity |
| --- | --- |
| 5-Oxo-2,2-pyrrolidinedipropanoic acid dibenzyl ester | 150 g |
| Lactose | 1124 g |
| Corn Starch | 39 g |
| Hydroxypropylcellulose | 30 g |
| Magnesium stearate | 7 g |
| Ethanol-water 50:50 | qs |

The 5-oxo-2,2-pyrrolidinedipropanoic acid dibenzyl ester, lactose, and hydroxypropylcellulose are blended and granulated with 50:50 ethanol-water. The wet granulation is screened, dried, and rescreened. The resulting dried granulation is blended with magnesium stearate and the corn starch and the mixture is compressed into 225 mg tablets using an 11/32 inch standard concave punch. Yield equals approximately 6000 tablets each containing 25.0 mg of 5-oxo-2,2-pyrrolidinedipropanoic acid dibenzyl ester.

EXAMPLE 13

| Ingredient | Quantity |
| --- | --- |
| 5-Oxo-2,2-pyrrolidinedipropanoic acid dibenzyl ester | 15 g |
| Lactose | 1249 g |
| Corn Starch | 39 g |
| Hydroxypropylcellulose | 30 g |
| Magnesium stearate | 7 g |
| Ethanol-water 50:50 | qs |

The 5-oxo-2,2-pyrrolidinedipropanoic acid dibenzyl ester, lactose, and hydroxypropylcellulose are blended and granulated with 50:50 ethanol-water. The wet granulation is screened, dried, and rescreened. The resulting dried granulation is blended with magnesium stearate and the corn starch, and the mixture is compressed into 225 mg tablets using an 11/32 inch standard concave punch. Yield equals approximately 600 tablets each containing 2.5 mg of 5-oxo-2,2-pyrrolidinedipropanoic acid dibenzyl ester.

EXAMPLE 14

| Ingredient | Quantity |
| --- | --- |
| 5-Oxo-2,2-pyrrolidinedipropanoic acid dibenzyl ester | 6 g |
| Lactose | 1268 g |
| Corn Starch | 39 g |
| Hydroxypropylcellulose | 30 g |
| Magnesium stearate | 7 g |
| Ethanol-water 50:50 | qs |

The 5-oxo-2,2-pyrrolidinedipropanoic acid dibenzyl ester, lactose, and hydroxypropylcellulose are blended and granulated with 50:50 ethanol-water. The wet granulation is screened, dried, and rescreened. The resulting dried granulation is blended with magnesium stearate and the corn starch, and the mixture is compressed into 225 mg tablets using an 11/32 inch standard concave punch. Yield equals approximately 6000 tablets each containing 1.0 mg of 5-oxo-2,2-pyrrolidinedipropanoic acid dibenzyl ester.

EXAMPLE 15

| Ingredient | Quantity |
| --- | --- |
| 5-Oxo-2,2-pyrrolidinedipropanoic acid dibenzyl ester | 300 g |
| Lactose | 974 g |
| Corn Starch | 39 g |
| Hydroxypropylcellulose | 30 g |
| Magnesium stearate | 7 g |
| Ethanol-water 50:50 | qs |

The 5-oxo-2,2-pyrrolidinedipropanoic acid dibenzyl ester, lactose, and hydroxypropylcellulose are blended and granulated with 50:50 ethanol-water. The wet granulation is screened, dried, and rescreened. The resulting dried granulation is blended with magnesium stearate and the corn starch, and the mixture is compressed into 225 mg tablets using an 11/32 inch standard concave punch. Yield equals approximately 6000 tablets each containing 50.0 mg of 5-oxo-2,2-pyrrolidinedipropanoic acid dibenzyl ester.

EXAMPLE 16

| Ingredient | Quantity |
| --- | --- |
| 5-Oxo-2,2-pyrrolidinedipropanoic acid dibenzyl ester | 250 g |
| Lactose | 1723 g |
| Magnesium stearate | 27 g |

The mixture is blended and filled into No. 4 hard gelatin capsules, filling each capsule with 200 mg of the powder mixture. Yield equals approximately 10,000 capsules each containing 25.0 mg of 5-oxo-2,2-pyrrolidinedipropanoic acid dibenzyl ester.

EXAMPLE 17

| Ingredient | Quantity |
| --- | --- |
| 5-Oxo-2,2-pyrrolidinedipropanoic acid dibenzyl ester | 25 g |
| Lactose | 1948 g |
| Magnesium stearate | 27 g |

The mixture is blended and filled into No. 4 gelatin capsules, filling each capsule with 200 mg of the powder mixture. Yield equals approximately 10,000 capsules each containing 2.5 mg of 5-oxo-2,2-pyrrolidinedipropanoic acid dibenzyl ester.

EXAMPLE 18

| Ingredient | Quantity |
| --- | --- |
| 5-Oxo-2,2-pyrrolidinedipropanoic acid dibenzyl ester | 500 g |
| Lactose | 1473 g |
| Maqnesium stearate | 27 g |

The mixture is blended and filled into No. 4 hard gelatin capsules, filling each capsule with 200 mg of the powder mixture. Yield equals approximately 10,000 capsules each containing 50.0 mg of 5-oxo-2,2-pyrrolidinedipropanoic acid dibenzyl ester.

EXAMPLE 19

| Ingredient | Quantity |
| --- | --- |
| 5-Oxo-2,2-pyrrolidinedipropanoic acid dibenzyl ester | 30 mg |
| Witepsol H 35 | 1.97 g |

The Witepsol H 35 is melted by heating to 38° C., 5-oxo-2,2-pyrrolidinedipropanoic acid dibenzyl ester is added and mixed until thoroughly dispersed and placed in a mold at 33°-34° C.

EXAMPLE 20

| Ingredient | Quantity |
| --- | --- |
| 5-Oxo-2,2-pyrrolidinedipropanoic acid dibenzyl ester | 10 g |
| Saccharin Sodium | 0.5 g |
| Trihydroxystearin | 0.75 g |
| Propylparaben | 0.1 g |
| Imitation Cherry flavor | 2 ml |
| Neobee M-5 q.s. ad | 100 ml |

The propylparaben is dissolved in a portion of the Neobee M-5, the trihydroxystearin is added and the mixture is homogenized for 30 minutes while maintaining the temperature between 50°–60° C. The mixture is cooled and the 5-oxo-2,2-pyrrolidinedipropanoic acid dibenzyl ester, saccharin sodium, and Imitation Cherry flavor are added. The volume is made up with Neobee M-5.

EXAMPLE 21

| Ingredient | Quantity |
| --- | --- |
| 5-Oxo-2,2-pyrrolidinedipropanoic acid dibenzyl ester | 10 g |
| Sugar granulated, Bottlers Grade | 60 g |
| Artificial Peppermint Flavor, Water Soluble | 0.4 g |
| Water q.s. ad | 100 ml |

The 5-oxo-2,2-pyrrolidinedipropanoic acid dibenzyl ester, granulated sugar and artificial peppermint flavor are dry blended. The blend is filled into a 4 oz bottle with a 100 ml calibration mark. At time of dispensing, make up to volume with water and shake until all of the solids are dissolved. The mixture is refrigerated and used within seven days.

I claim:
1. A compound having the structural formula

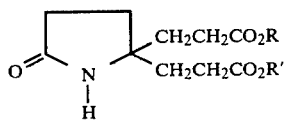

wherein R and R' are the same or different and are hydrogen;

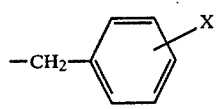

wherein X is hydrogen, alkyl of from one to six carbon atoms, alkoxy of from one to six carbon atoms, halo or trifluoromethyl; alkyl having from one to six carbon atoms;

or a pharmaceutically acceptable metal or amine cation; provided that R and R' may not both be hydrogen, ethyl, or different pharmaceutically acceptable metal or amine cations.

2. The compounds defined in claim 1 wherein R and R' are the same; provided they are not hydrogen or ethyl.

3. The compound defined in claim 1 having the name 5-oxo-2,2-pyrrolidinedipropanoic acid dibenzyl ester.

4. The compound defined in claim 1 having the name 5-oxo-2,2-pyrrolidindipropanoic acid disodium salt.

5. The compound defined in claim 1 having the name 5-oxo-2,2-pyrrolidinedipropanoic acid di-p-chlorobenzyl ester.

6. The compound defined in claim 1 having the name 5-oxo-2,2-pyrrolidinedipropanoic acid di-p-trifluoromethylbenzyl ester.

7. The compound defined in claim 1 having the name 5-oxo-2,2-pyrrolidinedipropanoic acid dimethyl ester.

8. The compound defined in claim 1 having the name of 5-oxo-2,2-pyrrollidinedipropanoic acid di-o-chlorobenzyl ester.

* * * * *